(12) United States Patent
Tam

(10) Patent No.: US 12,174,126 B2
(45) Date of Patent: *Dec. 24, 2024

(54) GEMSTONE TESTING APPARATUS

(71) Applicant: Jubilee Diamond Instrument(s) Pte. LTd., Singapore (SG)

(72) Inventor: Kui Lim Tam, Singapore (SG)

(73) Assignee: JUBILEE DIAMOND INSTRUMENT (S) PTE. LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 18/306,892

(22) Filed: Apr. 25, 2023

(65) Prior Publication Data

US 2023/0341331 A1 Oct. 26, 2023

Related U.S. Application Data

(63) Continuation of application No. 17/302,980, filed on May 18, 2021, now Pat. No. 11,668,654, which is a
(Continued)

(51) Int. Cl.
| | |
|---|---|
| *G01N 21/87* | (2006.01) |
| *G01N 21/33* | (2006.01) |
| *G01N 33/00* | (2006.01) |

(52) U.S. Cl.
CPC ............. *G01N 21/87* (2013.01); *G01N 21/33* (2013.01); *G01N 33/389* (2024.05); *G01N 2201/0221* (2013.01)

(58) Field of Classification Search
CPC ... G01N 21/87; G01N 21/59; G01N 2201/062
See application file for complete search history.

(56) References Cited

U.S. PATENT DOCUMENTS

| | | |
|---|---|---|
| 2,789,430 A | 4/1957 | Sinclaire |
| 4,255,962 A | 3/1981 | Ashman |
| | (Continued) | |

FOREIGN PATENT DOCUMENTS

| | | |
|---|---|---|
| JP | 2015194467 A | 11/2015 |
| WO | 8001414 A1 | 7/1980 |
| | (Continued) | |

OTHER PUBLICATIONS

International Preliminary Report on Patentability in related foreign application PCT/IB2017/050803. Dated Aug. 20, 2019. 12 pages.
(Continued)

*Primary Examiner* — Abdullahi Nur
(74) *Attorney, Agent, or Firm* — Thompson Patent Law Offices PC

(57) ABSTRACT

The application provides a gemstone testing apparatus for testing a specimen. The gemstone testing apparatus includes a handheld casing, a plurality of light sources, a test probe, a photodetector, a processor unit, and a display unit. The test probe is placed at one end of the handheld casing. A first end of the test probe is placed outside the handheld casing. The plurality of light sources is provided for emitting light rays towards an area that is in the vicinity of the first end. The first end is adapted for receiving light rays from the specimen and for transmitting the light rays to a second end of the test probe. The photodetector is arranged to measure an intensity of the light rays from the second end. The processor unit is provided for determining a material of the specimen in accordance to a measurement of the intensity of the light rays.

61 Claims, 11 Drawing Sheets

Figure 1:
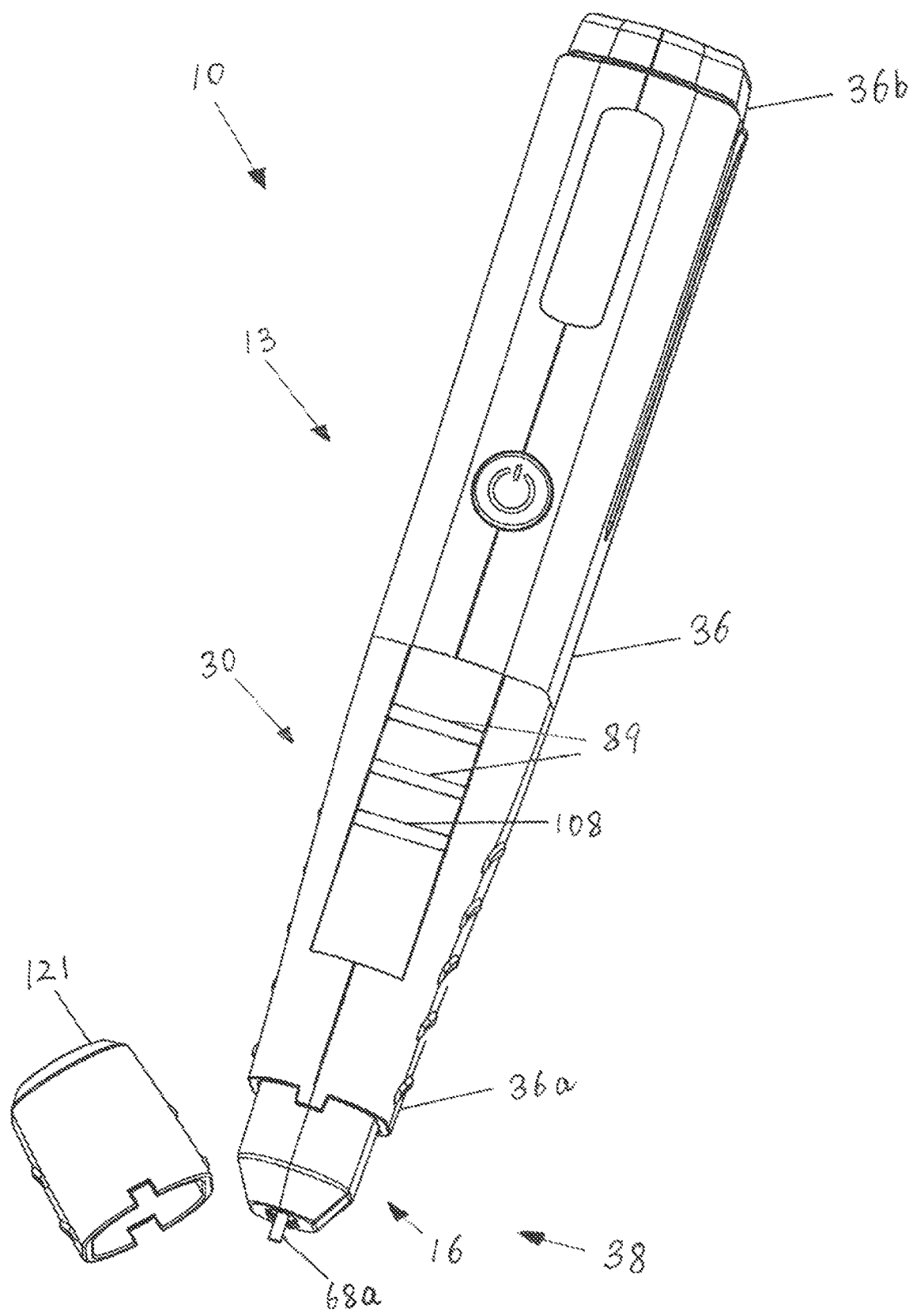

Related U.S. Application Data continuation of application No. 16/479,823, filed as application No. PCT/IB2017/058093 on Dec. 19, 2017, now abandoned.

(56) References Cited

U.S. PATENT DOCUMENTS

| | | | |
|---|---|---|---|
| 4,344,315 A | 8/1982 | Moxon et al. | |
| 4,364,677 A | 12/1982 | Ashman | |
| 4,394,580 A | 7/1983 | Gielisse | |
| 4,488,821 A | 12/1984 | Wenckus | |
| 5,164,586 A | 11/1992 | Hohberg et al. | |
| 5,801,819 A | 9/1998 | Spear et al. | |
| 5,835,205 A * | 11/1998 | Hunter | G01N 21/87 356/30 |
| 5,883,389 A | 3/1999 | Spear et al. | |
| 5,955,735 A | 9/1999 | Coleman | |
| 6,043,742 A | 3/2000 | Austin | |
| 6,265,884 B1 | 7/2001 | Menashi et al. | |
| 6,439,766 B1 | 8/2002 | Nelson | |
| 7,105,822 B1 | 9/2006 | Beesley | |
| 7,126,351 B2 * | 10/2006 | Claus | G01N 33/381 324/687 |
| 7,259,839 B2 | 8/2007 | Sivovolenko | |
| 7,362,109 B2 | 4/2008 | Loginov | |
| 7,382,445 B2 | 6/2008 | Sasian et al. | |
| 8,278,906 B2 | 10/2012 | Loginov et al. | |
| 8,564,316 B2 | 10/2013 | Kessler et al. | |
| 8,749,253 B2 | 6/2014 | Kessler et al. | |
| 8,760,758 B2 | 6/2014 | Verboven et al. | |
| 9,176,068 B1 | 11/2015 | Radomyshelsky et al. | |
| 9,395,350 B2 | 7/2016 | Kessler et al. | |
| 10,161,878 B2 | 12/2018 | Tam | |
| 10,228,330 B2 | 3/2019 | Tam | |
| 10,247,677 B2 | 4/2019 | Tam | |
| 10,837,915 B2 | 11/2020 | Tam | |
| 2001/0023925 A1 | 9/2001 | Smith | |
| 2004/0000888 A1 | 1/2004 | Shimada et al. | |
| 2005/0213203 A1 | 9/2005 | Harrison et al. | |
| 2006/0044823 A1 | 3/2006 | Wong et al. | |
| 2006/0087306 A1 | 4/2006 | Loginov | |
| 2006/0098187 A1 | 5/2006 | Claus | |
| 2007/0115653 A1 * | 5/2007 | Cea | A45C 15/06 362/104 |
| 2012/0007619 A1 * | 1/2012 | Zhu | G01N 27/041 324/717 |
| 2012/0049836 A1 | 3/2012 | Kessler et al. | |
| 2012/0059619 A1 | 3/2012 | Zhu et al. | |
| 2012/0274751 A1 | 11/2012 | Smith et al. | |
| 2014/0043011 A1 * | 2/2014 | Kessler | G01N 27/02 324/71.1 |
| 2014/0337035 A1 | 11/2014 | Kessler et al. | |
| 2015/0015877 A1 | 1/2015 | Smith et al. | |
| 2015/0021957 A1 | 1/2015 | Nellen et al. | |
| 2015/0091593 A1 | 4/2015 | Zhu et al. | |
| 2015/0219567 A1 | 8/2015 | Sim et al. | |
| 2016/0161420 A1 | 6/2016 | Zhu et al. | |
| 2016/0178168 A1 | 6/2016 | Didur | |
| 2016/0178530 A1 | 6/2016 | Davies et al. | |
| 2016/0290930 A1 | 10/2016 | Takahashi | |
| 2016/0363576 A1 | 12/2016 | Zhu et al. | |
| 2018/0238811 A1 | 8/2018 | Tam | |
| 2019/0011373 A1 | 1/2019 | Tam | |
| 2019/0072495 A1 | 3/2019 | Tam | |
| 2020/0249176 A1 | 8/2020 | Tam | |

FOREIGN PATENT DOCUMENTS

| | | |
|---|---|---|
| WO | 2014055041 A1 | 4/2014 |
| WO | 2015007873 A1 | 1/2015 |
| WO | 2017025825 A1 | 2/2017 |
| WO | 2017208053 A1 | 12/2017 |
| WO | 2018150221 A1 | 8/2018 |
| WO | 2018220572 A1 | 12/2018 |
| WO | 2019122955 A1 | 6/2019 |
| WO | 2019123293 A1 | 6/2019 |

OTHER PUBLICATIONS

Gems & Gemology; Article entitled: "Synthetic Moissanite: A New Diamond Substitute," published Winter 1997, 16 pgs.
Gems & Gemology; Symposium proceedings issue entitled: "Proceedings of the Third International Gemological Symposium," published Fall 1999, 185 pages.
In Related Foreign Application IN201947037061. Examination Report. Dated Feb. 25, 2021. 5 pages.
International Preliminary Report on Patentability in related foreign application PCT/IB2016/053208. Dated Nov. 13, 2018. 25 pages.
International Preliminary Report on Patentability in related foreign application PCT/IB2016/054071. Dated Dec. 21, 2017. 29 pages.
International Preliminary Report on Patentability in related foreign application PCT/IB2017/058093. Dated Jun. 23, 2020. 10 pages.
International Preliminary Report on Patentability in related foreign application PCT/IB2018/053881. Dated Aug. 26, 2019. 38 pages.
International Preliminary Report on Patentability in related foreign application PCT/IB2018/060308. Dated Jun. 23, 2020. 6 pages.
International Search Report in related foreign application PCT/IB2016/053208. Dated Jul. 12, 2017. 3 pages.
International Search Report in related foreign application PCT/IB2016/054071. Dated Feb. 16, 2017. 4 pages.
International Search Report in related foreign application PCT/IB2017/050803. Dated Aug. 23, 2018. 3 pages.
International Search Report in related foreign application PCT/IB2018/053881. Dated Dec. 6, 2018. 3 pages.
International Search Report in related foreign application PCT/IB2018/060308. Dated Jun. 29, 2019. 3 pages.
International Search Report in Related PCT Application No. PCT/IB2017/058093, dated Jun. 27, 2019, 9 pages.
Written Opinion in Related PCT Application No. PCT/IB2017/058093, dated Jun. 27, 2019, 3 pages.
Written Opinion of the International Searching Authority in related foreign application PCT/IB2016/053208. Dated Jul. 12, 2017. 9 pages.
Written Opinion of the International Searching Authority in related foreign application PCT/IB2016/054071. Dated Feb. 16, 2017. 7 pages.
Written Opinion of the International Searching Authority in related foreign application PCT/IB2017/050803. Dated Aug. 23, 2018. 11 pages.
Written Opinion of the International Searching Authority in related foreign application PCT/IB2018/053881. Dated Dec. 6, 2018. 17 pages.
Written Opinion of the International Searching Authority in related foreign application PCT/IB2018/060308. Dated Jun. 27, 2019. 5 pages.
ZEISS; Article entitled: "Education in Microscopy and Digital Imaging," published as early as Dec. 23, 2008, located at , 9 pages.
Office Action issued Mar. 27, 2024 by the China National Intellectual Property Administration in Application No. 201780098336.8, 9 pages.

* cited by examiner

GEMSTONE TESTING APPARATUS

CROSS-REFERENCE TO RELATED APPLICATIONS

This application is a Continuation of and claims the benefit of U.S. application Ser. No. 17/302,980, titled "GEMSTONE TESTING APPARATUS," filed by Kui Lim Tam on Mar. 18, 2021, which is a continuation of and claims the benefit of U.S. application Ser. No. 16/820,078, titled "GEMSTONE TESTING APPARATUS," filed by Kui Lim Tam on Mar. 16, 2020, which is a 371 (national stage entry) of PCT Application Serial No. PCT/IB2017/058093, titled "GEMSTONE TESTING APPARATUS" and filed Dec. 19, 2017. This application incorporates the entire contents of the foregoing application(s) herein by reference.

This application contains related subject matter by a common inventor with U.S. Ser. No. 15/751,529, titled "DIAMOND IDENTIFICATION APPARATUS," filed by Kui Lim Tam on Feb. 9, 2018; U.S. Ser. No. 16/496,721, titled "UV REFLECTION TESTER," filed by Kui Lim Tam on May 31, 2018; U.S. Ser. No. 16/128,610, titled "PRECIOUS STONE TESTING DEVICE," filed by Kui Lim Tam on Sep. 12, 2018; U.S. Ser. No. 16/176,059, titled "DIAMOND IDENTIFICATION APPARATUS," filed by Kui Lim Tam on Oct. 31, 2018; and, U.S. patent application Ser. No. 16/820,078, titled "GEMSTONE TESTING APPARATUS," filed by Kui Lim Tam on Mar. 16, 2020. This application incorporates the entire contents of the foregoing application(s) herein by reference.

The application relates to an apparatus for testing gemstones, namely diamond and moissanite.

Diamond includes a native crystalline carbon that is very hard. The diamond can have color or be colorless. When the diamond is transparent and free from flaws, it is highly valued as a jewelry. It is often used industrially as an abrasive.

Moissanite refers to a silicon carbide mineral and to its various crystalline polymorphs. The silicon carbide mineral can be found in nature, although this is rare. It can also be synthesized in the laboratory.

Synthetic moissanite, which is colorless or near-colorless, resembles diamond in many aspects, such as visual characteristics, hardness, and thermal conductivity among other physical properties. Therefore, synthetic moissanite is widely used as a diamond simulant in today's jewelry market.

A gemstone tester is often considered as a convenient tool for identifying gemstone, such as diamond, moissanite, and other precious stones. The gemstone tester can include a testing probe for determining thermal conductivity or electrical conductivity of the gemstone in order to classify the gemstone according to the thermal and electrical conductivity.

US20160363576A1 discloses a multi-functional precious stone testing apparatus that includes a portable housing, a testing unit, and an indication unit. The portable housing includes a hand-held casing and a probe casing. The probe casing extends from a front end of the hand-held casing. The testing unit includes a conductive probe. The conductive probe has a testing end portion that extends out of a tip end of the probe casing. The indication unit includes a LED light unit. The LED light unit is placed in the hand-held casing. The LED light unit is also positioned away from the tip end of the probe casing. Functionally, the conductive probe is intended for contacting a testing object to determine a conductivity of the testing object. The LED light unit, which is received in the hand-held casing, is used for illuminating the testing end portion of the conductive probe during testing. The LED light unit, which is also positioned away from the tip end of the probe casing, also acts to prevent heat, which is generated from the LED light unit, from being transmitted toward the conductive probe. The heat can affect an accuracy of measurement for the conductivity of the testing object.

U.S. Pat. No. 6,043,742A discloses an apparatus for detecting man-made gemstones using an alternating current conducted through a sample gemstone. The apparatus includes a hand-held housing in which is disposed electronic circuitry, a probe which extends from the housing, and a transmitting stimulus electrode in the form of a body-contact touchpad. The electronic circuitry includes a filter for eliminating non-transmitted signals sensed by the probe. In use, the operator probes the gemstone by touching the conductive probe to the gemstone in an attempt to sense signals conducted through the gemstone. The electronic circuitry is used for producing an alternating current signal, preferably in sine wave form, for delivery to the touchpad. The alternating current signal is transmitted through the operator of the apparatus into the sample gemstone. An alarm is activated upon the detection of the conducted transmitted signal, indicating that the gemstone is man-made.

It is an objective of the application to provide an improved gemstone testing apparatus.

The application provides an improved gemstone testing apparatus for testing a gemstone specimen in order to identify the material of the specimen. Examples of the gemstone specimen are diamonds and moissanites.

A thermal conductivity test is often used to separate diamond and moissanite from all other gemstones. Thereafter, the gemstone testing apparatus can be used to differentiate between diamond and moissanite.

The gemstone testing apparatus comprises a handheld casing, a plurality of light sources, a test probe, a photodetector, a processor unit, and a display unit.

The light sources, a part of the test probe, the photodetector, and the processor are often placed inside the handheld casing. The display unit are often placed on outer surface of the handheld casing.

The handheld casing acts to contain and protect inner parts of the gemstone testing apparatus. The shape of the handheld casing is designed for allowing a user to easily hold or carry the gemstone testing apparatus. The handheld casing can include grip indentations on an outer surface of the gemstone testing apparatus, thereby allowing the user to maintain a firm hold of the gemstone testing apparatus. The handheld casing is often made of plastic material to reduce weight and cost.

A first end of the test probe is placed outside the handheld casing. A second end of the test probe is often placed inside the handheld casing. In other words, the test probe protrudes from one part of the handheld casing.

The plurality of light sources is place on at least two sides of the test probe. The multiple light sources are provided for emitting ultraviolet (UW) light rays with a predetermined wavelength. The light sources are inclined at a predetermined angle in order to direct the light rays towards an area that is in the vicinity of the first end of the test probe. UV light rays normally refer to an electromagnetic radiation with a wavelength from about 10 nm to about 400 nm, although the workable range can be narrower.

The specimen is intended to be placed at this area for receiving the light rays. If the specimen is a diamond, it would reflect the light rays. If the specimen is a moissanite, it would absorb the light rays. In other words, the moissanite would not reflect the light rays.

In use, the test probe is placed near to the specimen. The first end of the test probe is adapted for receiving light rays from the specimen, which is illuminated by light rays from the multiple light sources. The test probe then transmits these light rays to the second end of the test probe.

The test probe is often provided with a light guide, such as a tube with a reflective inner surface. One end of the test probe is intended to receive light rays. An inner surface of the test probe then reflects and directs the light rays to another end of the test probe.

The photodetector is often placed near to the second end of the test probe. The photodetector is arranged to detect light rays from the light sources with the predetermined wavelength. These light rays travelled from the specimen, to the first end, to the second end of the test probe, and to the photodetector.

The photodetector is also arranged to measure a light intensity of these light rays.

The processor unit of an electronic testing unit is electrically connected to the plurality of light sources and to the photodetector. The processor unit is provided for determining a material of the gemstone in accordance to a measurement of the light intensity of the light rays. In other words, the processor unit determines whether the specimen comprises a diamond or a moissanite.

If the processor unit determines that the specimen reflects light rays, then the processor unit considers the specimen is a diamond. On the other hand, if the processor unit determines that the specimen does not reflect light rays, then the processor unit considers the specimen is a moissanite.

The display unit is electrically connected to the processor unit. The display unit is used for receiving a data regarding the determination of the material of the gemstone specimen from the processor unit. The display unit then shows or displays this data.

The plurality of light sources provides benefits.

The arrangement of the multiple light sources allows a table of the specimen to receive light rays while the test probe is placed at different parts of the table of the specimen, even at an edge of the table. The table refers to a flat facet on the top of a gemstone specimen. This flat facet is often the largest facet of a cut specimen.

In practice, the size of the test probe is often smaller than the size of the table of the specimen. A user may place the test probe at different parts of the table of the specimen.

When the test probe is placed substantially near or at the center location of the table, the table of the specimen would receive light rays emitted from all multiple light sources.

When the test probe is not placed substantially near the center location of the table of the specimen, such as at the edge of the table, the table of the specimen would still receive light rays emitted from one or more of the multiple light sources.

In short, the multiple light sources allow the specimen to receive sufficient light rays for testing the specimen, even when the test probe is placed at different parts of the table of the gemstone. The user is not restricted to place the test probe at the center of the table in order to obtain an accurate gemstone test result.

This is different from other gemstone tester with a test probe and with just one single light source being placed at one side of the test probe.

When the test probe is placed near or at a center location of a table of a specimen, the table of the specimen would receive light rays from the single light source.

When the test probe is placed at an edge of the table of the specimen, only a side facet of the specimen may receive light rays from the single light source. In other words, no light rays or little light rays are directed onto the table of the specimen.

The table of the specimen may then not receive enough light rays for testing the specimen. This then degrades or affects the testing to the specimen.

The gemstone testing apparatus can have different aspects.

In one implementation, the plurality of light sources of the gemstone testing apparatus comprises two light sources, although it can also comprise three or more light sources.

In a further implementation, the plurality of light sources is arranged around the test probe in a symmetric manner. In other words, the multiple light sources serve as similar parts that face each other or around a longitudinal axis of the test probe. In one example, two light sources are placed at two opposing sides of the test probe.

Each of the light sources is often inclined at a predetermined angle with respect to the longitudinal axis of the test probe.

The gemstone testing apparatus often includes a pressure switch and a pressure transmitting means.

In use, the test probe is brought in contact with a gemstone specimen and it is pressed against a table or a surface of the gemstone specimen. The pressing acts for transferring a force from the gemstone specimen to the test probe. The pressure transmitting means acts to transfer the force from the test probe to the pressure switch. Upon receiving the force from the pressure transmitting means, the pressure switch then transmits a signal to activate or power up the processor unit of the gemstone testing apparatus. The activated processor unit thereafter provides electrical power to the multiple light sources for illuminating the gemstone specimen for testing the specimen.

The pressure switch together with the pressure transmitting means allows the multiple light sources to be powered up only when the gemstone testing apparatus is activated by the test probe pressing against the gemstone specimen. This thereby saves power. This is especially important when the gemstone testing apparatus is powered by a battery.

As an example, the pressure transmitting means includes an actuator member that comprises a rod-like member. The rod-like member can also operate with a spring member. In use, when the actuator member is moved by the test probe, the actuator member shifts towards the pressure switch, wherein the actuator member pushes an on/off button of the pressure switch for activating the processor unit of the gemstone testing apparatus.

In one implementation, the pressure switch is provided in the form of a micro-switch. The micro-switch is normally in an open position. Upon receiving a force from the pressure transmitting means, the micro-switch changes to a closed position. The micro-switch provides a switch position signal to the processor unit for activating or powering up the processor unit in order to enable the gemstone testing apparatus to test the gemstone specimen.

In one aspect of the application, the multiple light sources of the gemstone testing apparatus emit light rays with a fixed wavelength that is between about 315 nm and about 400 nm while the photodetector is configured to detect light rays with this fixed wavelength. In other words, the photodetector with a peak detection sensitivity that is suitable for detecting light rays with this fixed wavelength.

Alternatively, the light rays can also have different wavelengths that are between about 315 nm and about 400 nm. The photodetector is then configured to detect light rays with these different wavelengths.

In one specific implementation, the multiple light sources emit light rays with a fixed wavelength of about 365 nm. The photodetector is configured to detect light rays with this fixed wavelength of about 365 nm.

In a different implementation, the plurality of light sources is replaced with a ring light. The ring light is arranged to surround the test probe. The ring light is used for emitting light rays from different sides of the test probe, wherein the light rays are directed towards the gemstone specimen.

The gemstone testing apparatus often includes an external cap that is intended for attaching to the handheld casing in order to cover and to protect the test probe from being damaged.

The external cap can further comprise a gemstone test reference tablet. The gemstone test reference tablet is capable of reflecting light rays from the multiple light sources. In use, a user uses the gemstone test reference tablet to check functions of the gemstone testing apparatus.

The gemstone testing apparatus often includes a power source unit for supplying electrical power to parts of the gemstone testing apparatus, such as the multiple light sources, the photodetector, the electronic testing unit, and the display unit.

The gemstone testing apparatus can provide gemstone test results to the user in different ways.

In one implementation, the display unit of the gemstone testing apparatus includes a plurality of indicator lights for providing visual indications of the gemstone test results. In other words, the display unit can include indicator lights or a display screen for emitting light rays to visually display data regarding the gemstone test results.

In another implementation, the gemstone testing apparatus further includes a buzzer or an audio speaker for generating an audio indication of the gemstone test result. An example of the audio indication includes a continuous or an intermittent beeping sound.

In another aspect of the application, the test probe includes a hollow light guide with a reflective inner surface. The reflective inner surface serves to reflect and direct light rays from one end to another end of the light guide.

In one specific implementation, the hollow light guide includes a metal tube.

The application also provides a method for differentiating between a diamond and a moissanite.

The method includes a step of a user pressing a test probe of the gemstone testing apparatus against a table of a gemstone specimen. A force is then transmitted from the gemstone to the test probe and to a pressure switch of the gemstone testing apparatus.

After this, a plurality of light sources of the gemstone testing apparatus is activated for illuminating the gemstone specimen with light rays. The table of the gemstone specimen receives the light rays from at least one of the multiple light sources.

If the gemstone specimen is a moissanite, the light rays are then absorbed. In other words, essentially no light rays are reflected from the moissanite. If the gemstone specimen is a diamond, the light rays are reflected to the test probe. An intensity of the light rays being reflected from the gemstone specimen is afterward measured. A material of the gemstone is later determined in accordance to the measured light intensity.

The method can include a further step of providing an indication of the material of the gemstone specimen to a user.

In one implementation, said step of providing the indication of the material of the gemstone specimen comprises a plurality of light indicators providing a visual indication of the determined material of the gemstone specimen.

In another implementation, said step of providing the indication of the material of the gemstone specimen comprises a buzzer or speaker generating an audio indication of the determined material of the gemstone specimen.

Figure 2:
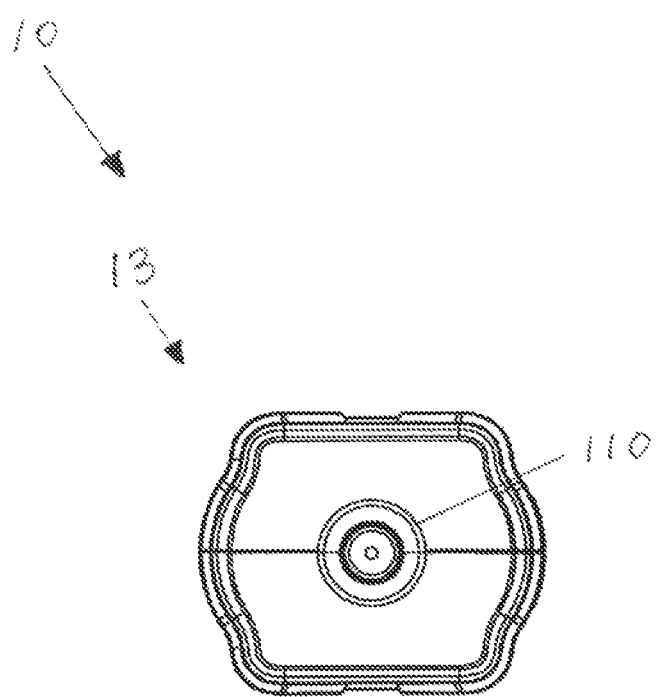
Figure 3:
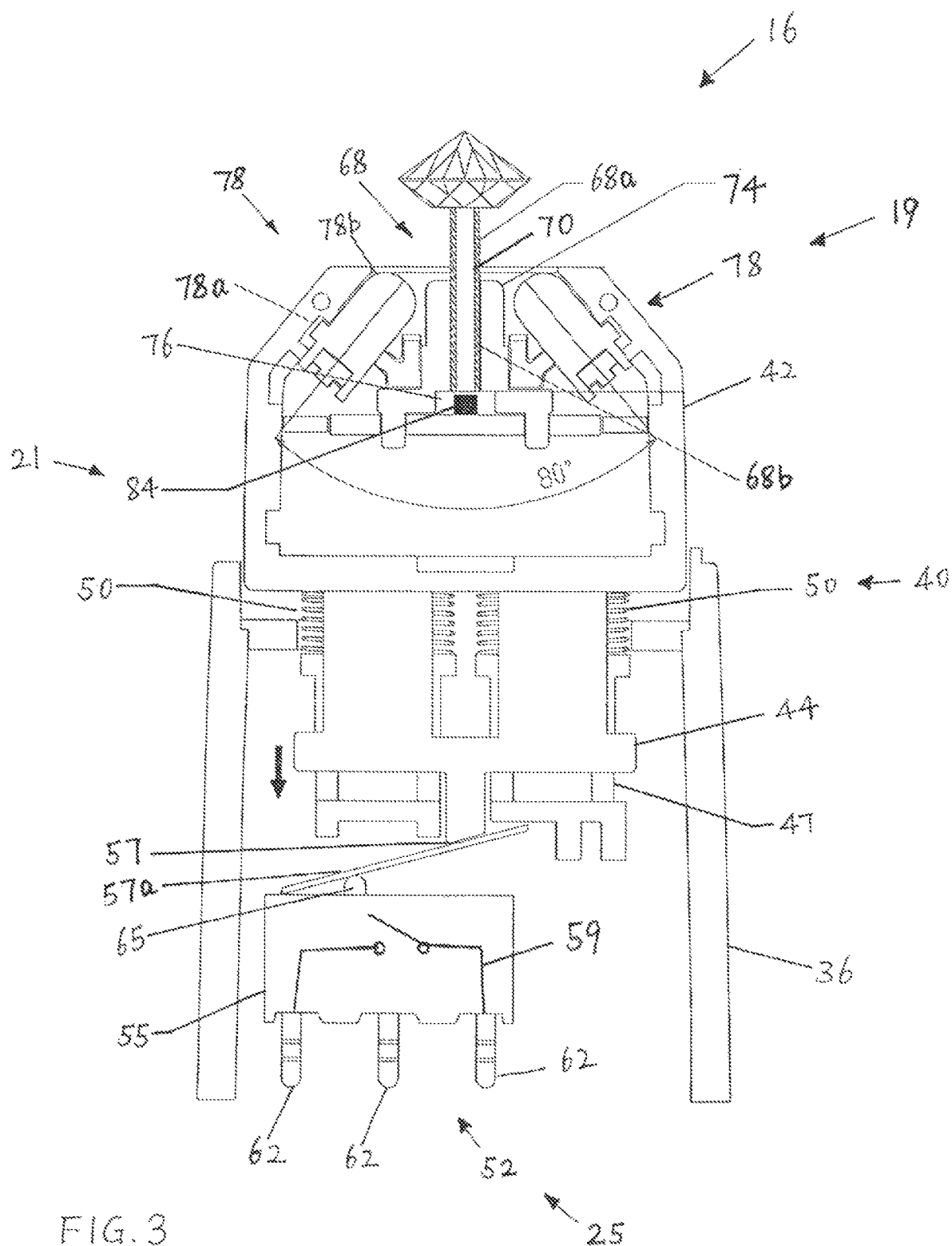
Figure 4:
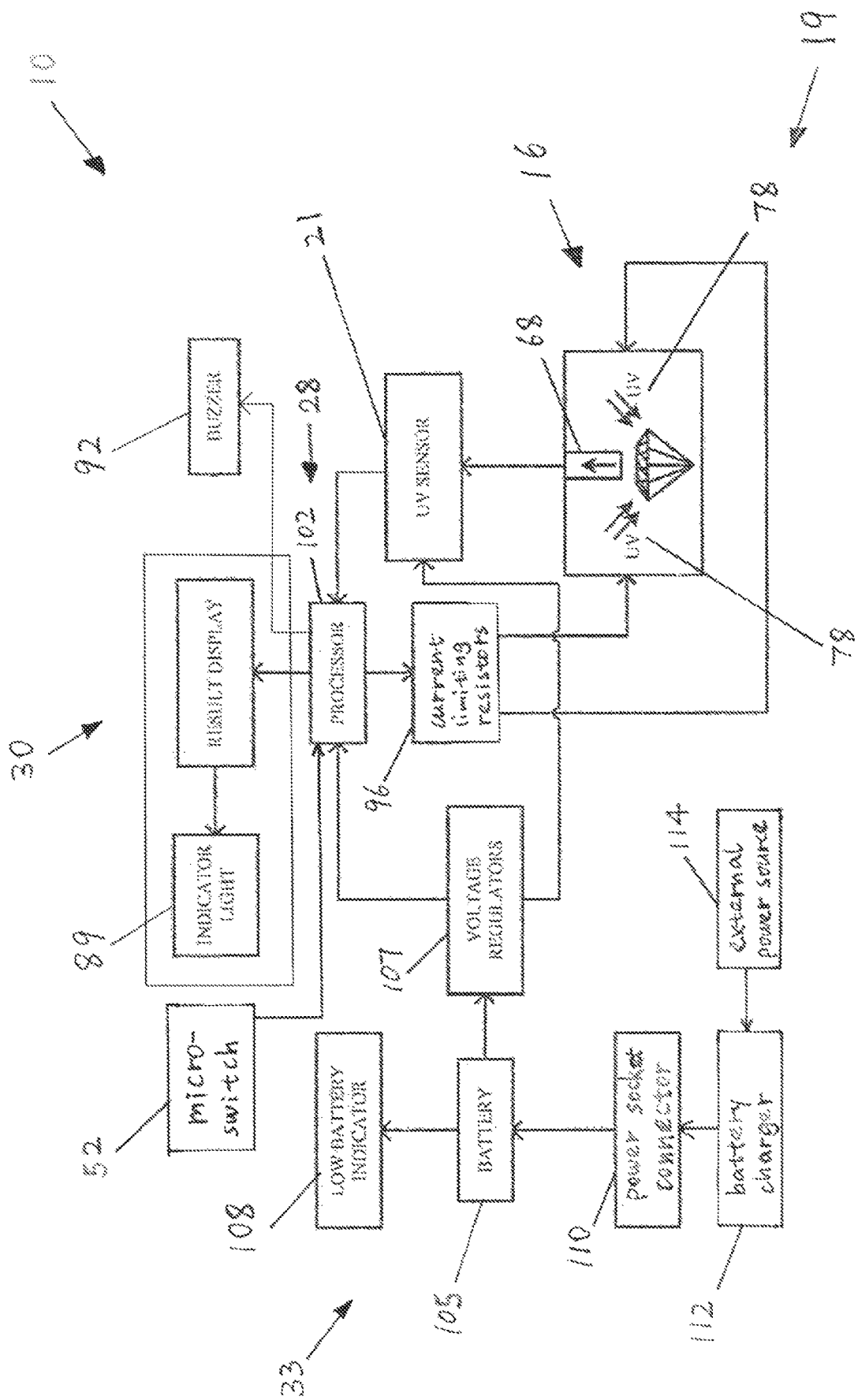
Figure 5:
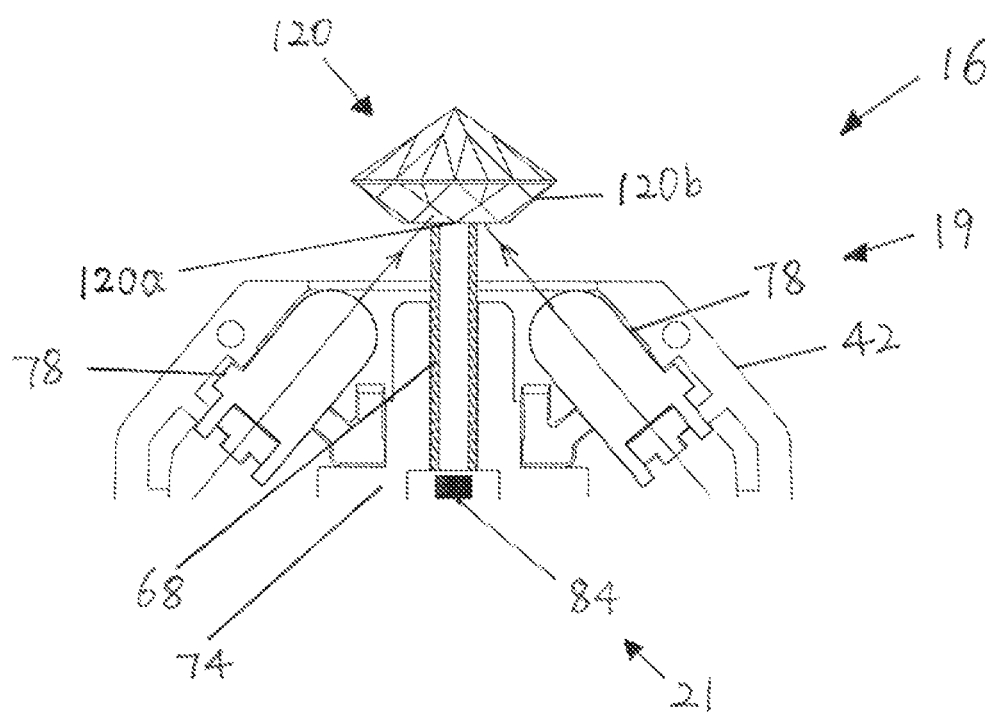
Figure 6:
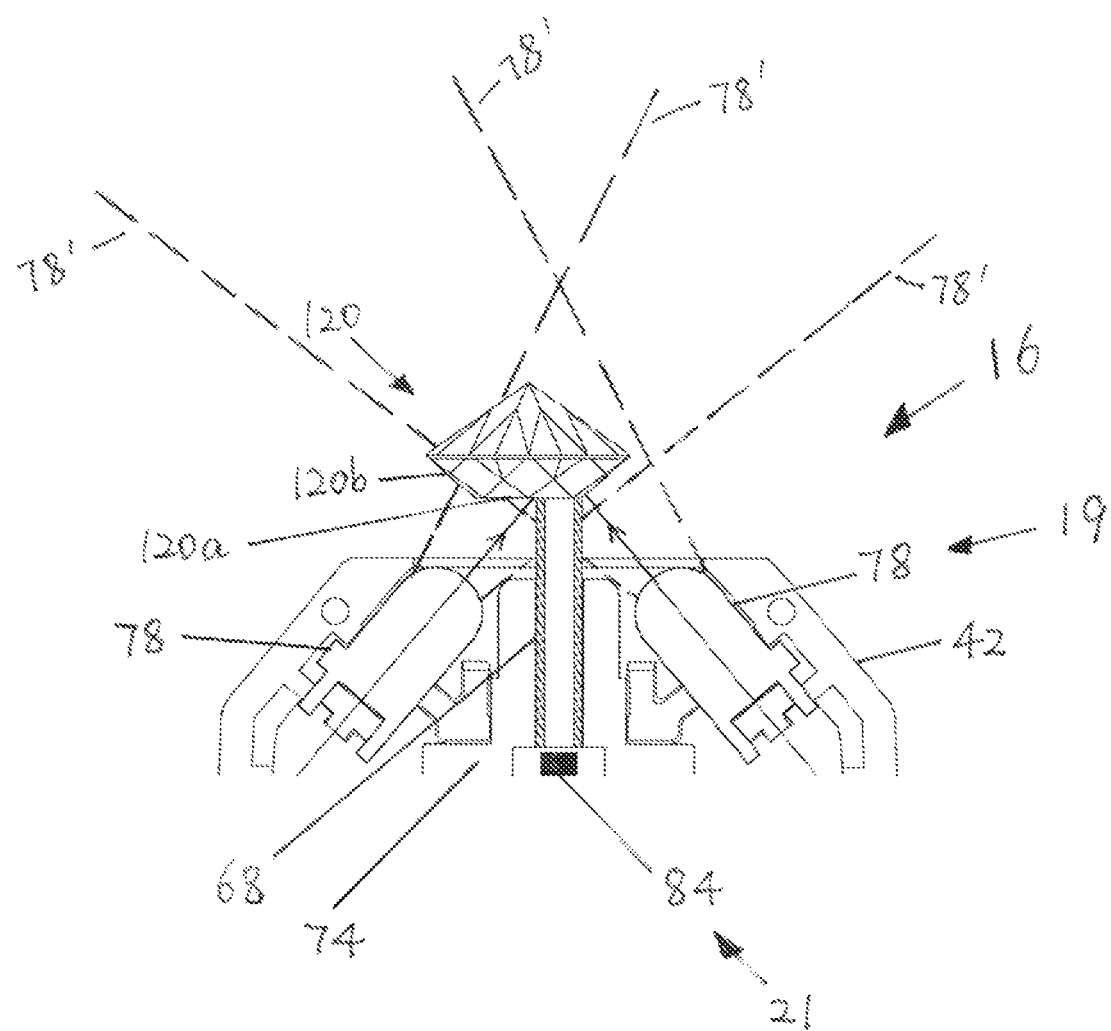
Figure 7:
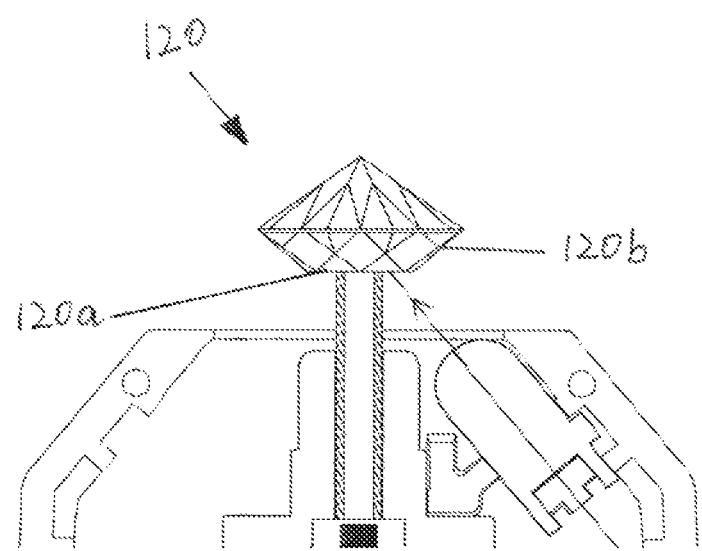
Figure 8:
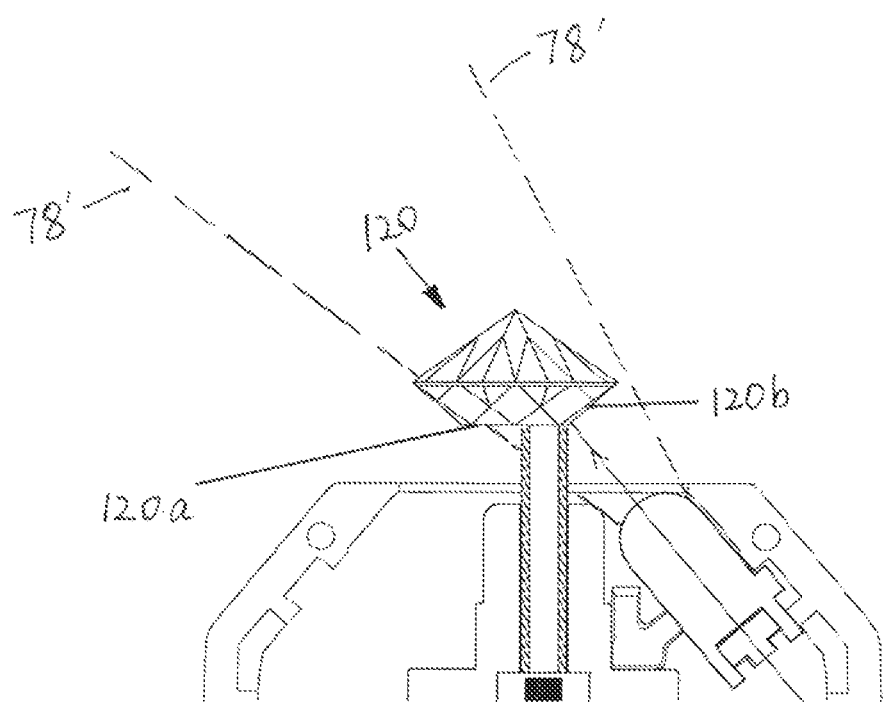
Figure 9:
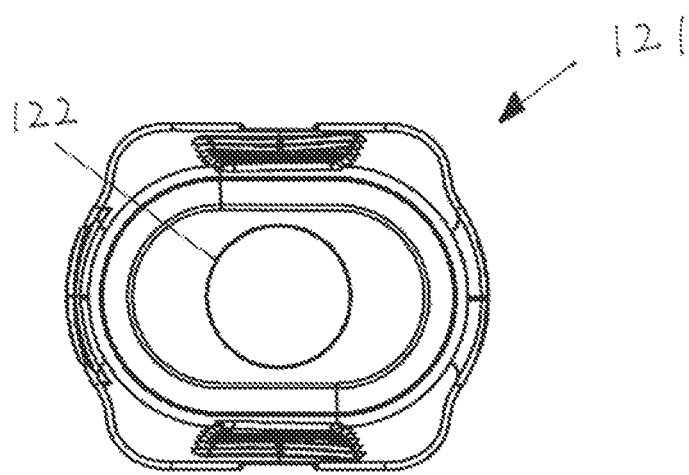
Figure 10:
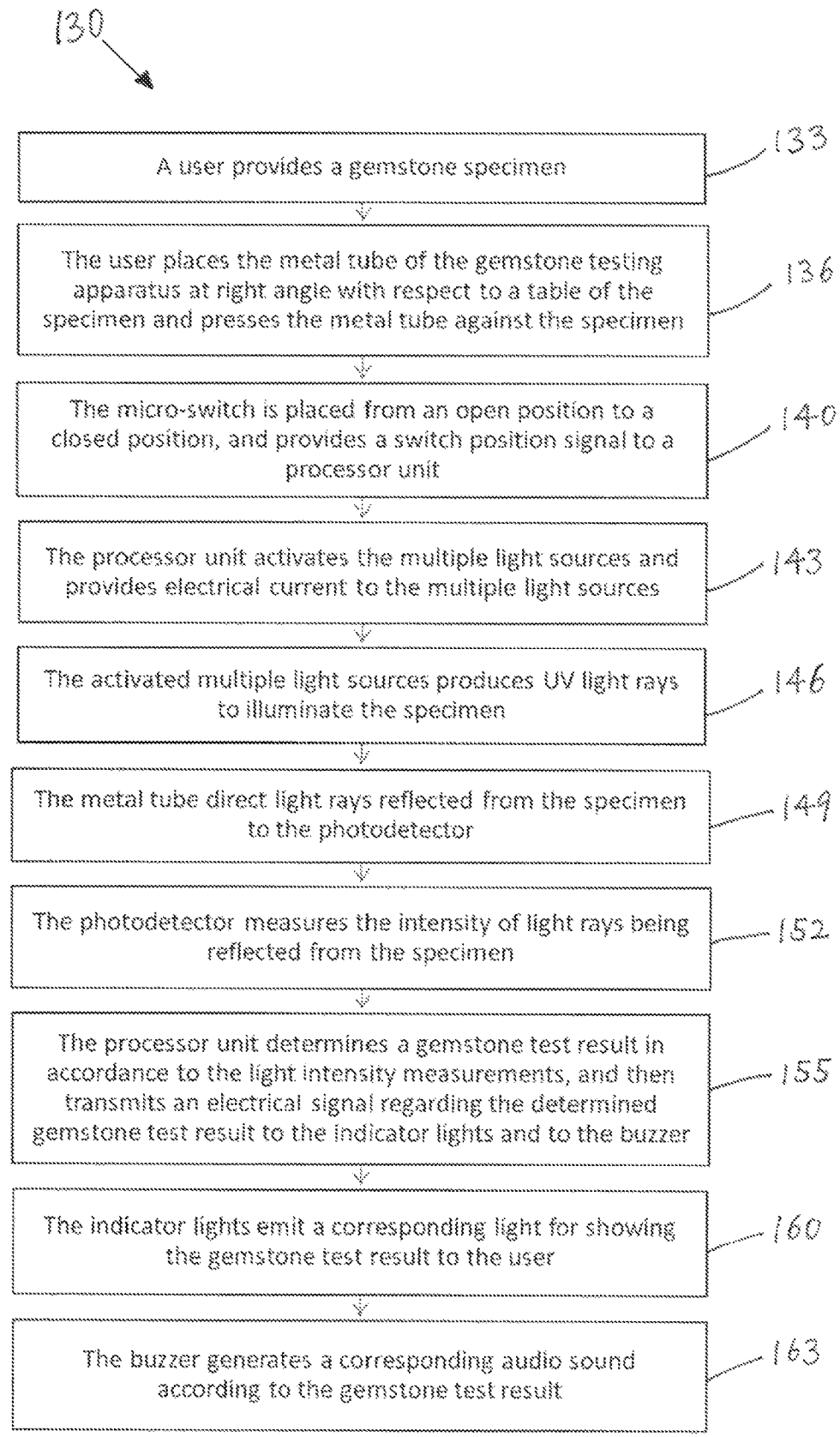
Figure 11:
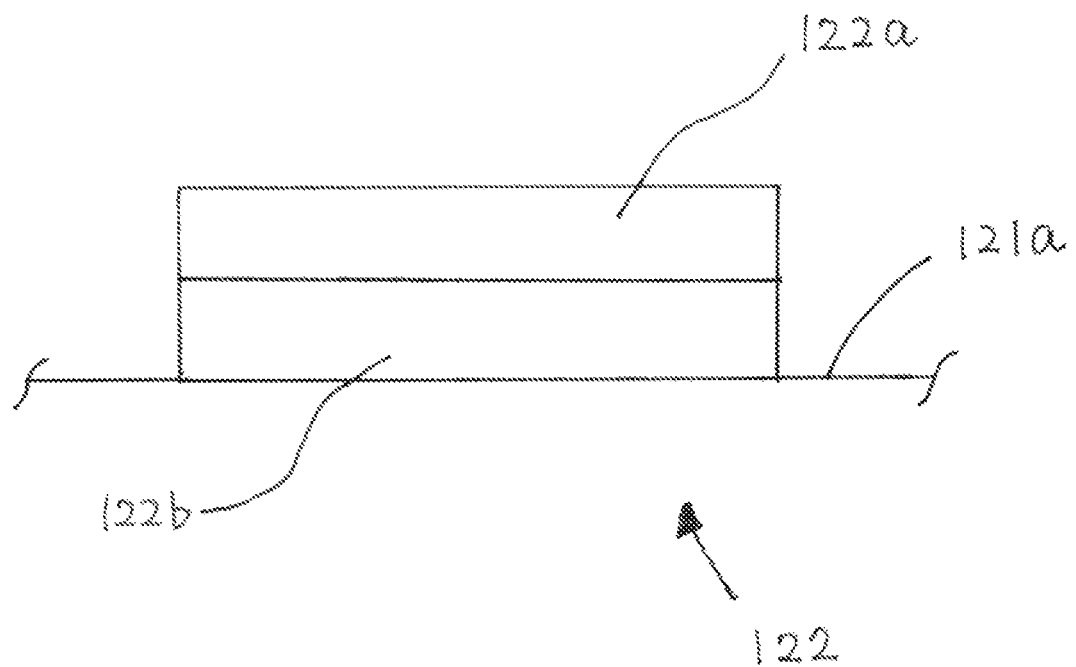

The subject matter of the application is described in greater detail in the accompanying Figures, in which FIG. 1 illustrates a perspective view of an improved gemstone testing apparatus, FIG. 2 illustrates a rear view of the gemstone testing apparatus of FIG. 1, FIG. 3 illustrates a partial cross-sectional view of a head portion of the gemstone testing apparatus of FIG. 1, FIG. 4 illustrates an electronic block diagram of the gemstone testing apparatus of FIG. 1, FIG. 5 illustrates a partial cross-sectional view of the head portion of the gemstone testing apparatus of FIG. 1, wherein a metal tube of the gemstone testing apparatus is placed at a center portion of a table of a specimen, FIG. 6 illustrates a partial cross-sectional view of the head portion of the gemstone testing apparatus of FIG. 1, wherein the metal tube is placed at an edge of the table of specimen, FIG. 7 illustrates a partial cross-sectional view of a head portion of another gemstone tester with a single light source, wherein a test probe of the gemstone tester is placed at a center portion of the table of the specimen, FIG. 8 illustrates a partial cross-sectional view of the head portion of the gemstone testing apparatus of FIG. 7, wherein the test probe is placed at an edge of the table of specimen, FIG. 9 illustrates a top view of an external cap with a gemstone test reference tablet for the gemstone testing apparatus of FIG. 1, FIG. 10 illustrates a flow chart of steps of a method of operating the gemstone testing apparatus of FIG. 1, and FIG. 11 illustrates a partial side view of the gemstone test reference tablet of FIG. 9.

In the following description, details are provided to describe the embodiments of the specification. It shall be apparent to one skilled in the art, however, that the embodiments may be practiced without such details.

Some parts of the embodiments have similar parts. The similar parts may have the same names or similar part numbers with an alphabet symbol or prime symbol. The description of one part applies by reference to another similar part, where appropriate, thereby reducing repetition of text without limiting the disclosure.

FIGS. 1 to 3 show an improved gemstone testing apparatus 10 to differentiate between diamond and moissanite.

In use, a gemstone specimen is often subjected to a thermal conductivity test. If the thermal conductivity test indicates that the specimen can be a moissanite or a diamond, the gemstone testing apparatus 10 is then used to determine whether the specimen is a moissanite or a diamond.

The gemstone testing apparatus 10 comprises an elongated handheld casing 13, a test probe 16 with a light module 19 together with a photodetector 21, a pressure switch 25, an electronic testing unit 28, a display unit 30 together with a buzzer 92, and a power source unit 33. The electronic testing unit 28 is also called a testing electronic circuit. The photodetector 21 is also called an ultra-violet (TJV) sensor.

The test probe 16 is also called a detector probe. The handheld casing 13 is also called an apparatus body. The power source unit 33 is also called a power source for short.

A part of the test probe 16, the light module 19, the photodetector 21, the pressure switch 25, the electronic testing unit 28, a part of the power source unit 33, and the buzzer 92 are placed inside the elongated handheld casing 13. The display unit 30 is placed on an outer surface of the elongated handheld casing 13. The electronic testing unit 28 is electrically connected to the power source unit 33, to the light module 19, to the photodetector 21, to the pressure switch 25, to the display unit 30, and to the buzzer 92. The electronic testing unit 28 is soldered on a printed circuit board (PCB).

The handheld casing 13 includes an elongated hollow body portion 36, a head portion 38, and a spring support unit 40.

The elongated hollow body portion 36 essentially has a shape of a cylinder. The elongated hollow body portion 36 has a first end 36a and a second end 36b, which is positioned opposite to the first end 36a. The head portion 38 is positioned next to the first end 36a of the elongated hollow body portion 36. A longitudinal axis of the elongated hollow body portion 36 is aligned with a longitudinal axis of the head portion 38. The spring support unit 40 is placed inside the elongated hollow body portion 36 and is attached to the head portion 38.

The head portion 38 includes a hollow conical member 42 with an actuator member 44 and a support member 47. The actuator member 44 is integrally connected to the hollow conical member 42. The hollow conical member 42 is placed next to the first end 36a of the hollow body portion 36 of the handheld casing 13. The actuator member 44 and the support member 47 are placed inside the first end 36a of the hollow body portion 36. The actuator member 44 is movably connected to the support member 47. The support member 47 is fixed to the hollow body portion 36 of the handheld casing 13.

The spring support unit 40 includes a plurality of coil torsion springs 50. Parts of the actuator member 44 are inserted into the coil torsion springs 50. The coil torsion springs 50 are adapted for pushing the support member 47 away from the hollow conical member 42.

The pressure switch 25 includes a mechanical micro-switch 52. The micro-switch 52 includes a rectangular body 55, an offset lever 57, and a single throw and single pole (STSP) switch 59, three electrical terminals 62. The STSP switch 59 includes an on/off button 65. One end of the offset lever 57 is movably attached to the rectangular body 55. A middle portion 57a of the offset lever 57 is placed next to the on/off button 65. Two ends of the STSP switch 59 are electrically connected to two of the electrical terminals 62. The offset lever 57 is placed adjacent to one end of the actuator member 44. The electrical terminals 62 are electrically connected to the electronic testing unit 28.

The test probe 16 includes a metal tube 68 with a reflective inner surface 70 together with a protective shell 74. A first end 68a of the metal tube 68 protrudes from the head portion 38 and is placed outside the head portion 38. The protective shell 74 surrounds a second end 68b of the metal tube 68 and it touches the second end 68b of the metal tube 68. The protective shell 74 also provides a cavity 76 that is placed next to the second end 68b of the metal tube 68.

As seen in FIG. 3, the light module 19 includes two light sources 78. The light sources 78 are positioned near to the test probe 16 and they are also placed around the test probe 16 in a symmetrical manner. The light sources 78 are placed opposite to each other. Each light source 78 includes a cylindrical body 78a and a semi-spherical part 78b that is placed at one end of the cylindrical body 78a. The cylindrical body 78a is inclined at an angle of about 40 degrees with respect to the longitudinal axis of the metal tube 68 and it is pointing towards a predetermined location that is positioned near to the first end 68a of the metal tube 68. The light sources 78 are electrically connected to the electronic testing unit 102 via current limiting resistors 96. Each light source 78 includes one ultraviolet (UV) Light Emitting Diode (LED).

The photodetector 21 includes a photodiode 84. The photodiode 84 is placed adjacent to the second end 68b of the metal tube 68 and it is placed inside the cavity 76 that is formed by the protective shell 74. The photodiode 84 is also positioned along a longitudinal axis of the metal tube 68. The size of the photodiode 84 is comparable with the size of a diameter of the second end 68b of the metal tube 68.

The photodetector 21 has a peak detection sensitivity that corresponds with the wavelength of the ultraviolet light rays from the light sources 78. The photodetector 21 is also electrically connected to the electronic testing unit 28.

The chamber, that is formed by the protective shell 74, acts to allow only the reflected light rays from the metal tube 68 to reach the photodetector 21 while prevent other light rays from reaching the photodetector 21.

The display unit 30 comprises multiple indicator lights 89 together with a low battery indicator 108. The indicator lights 89 and the low battery indicator 108 are disposed on an outer surface of the hollow body portion 36 of the handheld casing 13. The display unit 30 is electrically connected to the electronic testing unit 28.

The buzzer 92 is placed inside the hollow body portion 36 of the handheld casing 13. The buzzer 92 is also electrically connected to the electronic testing unit 28.

As shown in FIG. 4, the electronic testing unit 28 includes a processor unit 102. The photodetector 21 and the light sources 78 together with the indicator lights 89, the low battery indicator 108, and the buzzer 92 of the display unit 30 are electrically connected to the processor unit 102.

The power source unit 33 comprises a battery module 105 with a voltage regulator 107, a power socket connector 110, and a battery charger 112. The battery module 105, and the voltage regulator 107 are placed inside the hollow body portion 36. The power socket connector 110 is partially enclosed in the hollow body portion 36 and is placed at the second end 36b of the hollow body portion 36. The battery charger 112 is adapted for electrically connecting to an external power source 114 and for electrically connecting to the power socket connector 110. The power socket connector 110 is electrically connected to the battery module 105. The battery module 105 and the voltage regulator 107 are adapted for providing electrical power to electronic components of the electronic testing unit 28. The battery module 105 includes a lithium battery that is electrically connected to contact terminals that are soldered onto a printed circuit board (PCB).

In one implementation, the metal tube 68 has a length of about 9.30 millimeter (mm).

In a special implementation, the light source 78 produces a UV light with a wavelength of about 365 nm. The photodetector 21 has a peak detection sensitivity at about 365 nm.

The indicator lights 89 may be provided by LEDs with suitably chosen colors.

Functionally, the gemstone testing apparatus 10 provides a way to differentiate between diamond and moissanite.

In use, a thermal conductivity test can be used to separate diamond and moissanite from all other gemstones. Thereafter, the gemstone testing apparatus 10 can be used to differentiate between diamond and moissanite.

The gemstone testing apparatus 10 is intended to be held by a user such that the first end 68a of the metal tube 68 is placed on the surface of a specimen.

The user then presses the metal tube 68 against the specimen. The hollow conical member 42 with the actuator member 44 then moves into the body portion 36, along the longitudinal axis of the elongated body portion 36 by a substantially small distance. The hollow conical member 42 with the actuator member 44 also move towards the micro-switch 52. This movement acts to compress the springs 50.

The actuator member 44 afterward pushes the offset lever 57 of the micro-switch 52 such that the offset lever 57 pushes the on/off button 65 of the micro-switch 52 into the rectangular body 55 of the micro-switch 52.

The micro-switch 52 can be placed in a closed and a normally open position. The above pushing of the on/off button 65 acts to place the micro-switch 52, from the open position, to the closed position. The micro-switch 52 also acts to provide a switch position signal to the processor unit 102.

The current limiting resistor 96 acts to regulate electrical current to the light sources 78, when the light sources 78 are activated by the processor unit 102.

The activated light sources 78 produce ultraviolet light rays. The ultraviolet light rays are intended for illuminating a specimen, which is placed near to the test probe 16, when it is activated by the processor unit 102. The light ray is also called light for short.

The ultraviolet light rays have a predetermined fixed wavelength that is within a predetermined UV light spectrum band. The ultraviolet light rays can also have different wavelengths that are within the predetermined UV light spectrum band. In one implementation, the predetermined UV light spectrum band is between about 315 nm and about 400 nm.

As seen in FIGS. 5 and 6, the two light sources 78 allow a table 120a of the specimen 120 to receive light from either one or two of the light sources 78, when the metal tube 68 is placed at different parts of the table 120a, such as an edge of the table 120a.

In practice, the size of the metal tube 68 is often smaller than the size of the table 120a of the specimen 120. Because of this, a user may place the metal tube 68 at different parts of the table 120a of the specimen 120. The metal tube 68 can be placed near to a center location or be placed at an edge of the table.

The table 120a of the specimen 120 refers to a flat facet on the top of a gemstone specimen 120. One example of the specimen 120 is a diamond or moissanite. The flat facet is usually the largest facet of a cut specimen.

When the metal tube 68 is placed substantially near or at the center location of the table 120a of the specimen 120, the table 120a of the specimen 120 would receive light emitted from both light sources 78, as illustrated in FIG. 5.

When the metal tube 68 is not placed substantially near the center location of the table 120a of the specimen 120, such as the edge of the specimen 120, the table 120a of the specimen 120 would still receive light emitted from one of the two light sources 78. This illustrated by ray lights with borders 78' in FIG. 6.

In short, the two light sources allow the table 120a of the specimen 120 to receive light rays from the light sources even when the metal tube 68 is placed at different parts of the table 120a of the specimen 120.

This is different from other gemstone tester with a test probe tube and with just one single light source.

When the test probe tube is placed near or at a center location of a table 120a of a specimen 120, the table 120a would receive light rays from the single light source, as shown in FIG. 7.

When the probe tube is placed at an edge of the table 120a of the specimen 120, only a side facet 120b of the specimen 120 may receive light rays from the single light source, as shown in FIG. 8. In other words, no light rays or little light rays are directed onto the table 120a of the specimen.

The specimen 120 may then not receive enough light rays for testing the specimen 120. This then degrade or affect the testing to the specimen 120.

Referring to the specimen 120, it can include a moissanite or to a diamond. If the specimen 120 includes a moissanite, the moissanite would absorbs these light rays from the light sources 78. In other words, no light rays are reflected from the moissanite. If the specimen 120 includes a diamond, the diamond would reflect the light rays or reflect part of the light rays from the light sources 78.

The metal tube 68 acts as a light guide to receive the light rays reflected from the specimen 120. In detail, the second end 68b of the metal tube 68 receives the light rays reflected from the specimen 120. The inner surface of the metal tube 68 then reflects these light rays without absorbing these light rays. The inner surface also directs these light rays to the second end 68b of the metal tube 68 and towards the photodetector 21.

Referring to the protective shell 74, it provides a structural support for the two light sources 78 and for the metal tube 68, preventing them from moving.

The photodetector 21 detects and measures intensity of light rays being reflected from the specimen. The photodetector 21 then sends the light measurements to the processor unit 102.

The indicator lights 89 receives an electrical signal regarding a gemstone test result from the processor unit 102 and then emits a corresponding light for showing the gemstone test result to a user. As an example, the indicator lights 89 activates a first LED for showing that the gemstone testing apparatus detects a diamond. The indicator lights 89 activates a second LED for showing that the gemstone testing apparatus detects a moissanite.

The buzzer 92 also receives a signal from the processor unit 102 and generates a corresponding audio sound in accordance to the signal. The buzzer 92 produces a continuous beeping sound when the gemstone testing apparatus 10 detects a diamond. The buzzer 92 produces a short intermittent beeping sound when the gemstone testing apparatus 10 detects a moissanite.

After the indicator lights 89 emits a light for showing the gemstone test result to the user, the user can remove the metal tube 68 away from the specimen 120.

The coil torsion springs 50 then pushes the hollow conical member 42 and the actuator member 44 away from the micro-switch 52.

The actuator member 44 afterward does not push and does not contact the offset lever 57 of the micro-switch 52.

The micro-switch 52 then returns to its open position from its closed position. The micro-switch 52 then provides a switch position signal to the processor unit 102.

The battery module 105 supplies electrical power to the light sources 78, to the electronic testing unit 28, and to the display unit 30.

The voltage regulator 107 allows the battery module 105 to provide an output voltage with a constant voltage level.

The battery charger 112 together with the power socket connector 110 is used for connecting to an external power source 114. The connecting allows the external power source 114 to charge the battery module 105. The charging provides electrical energy to the battery module 105.

The processor unit 102 includes a program or instructions to receive a switch position signal from the micro-switch 52. After this, the processor unit 102 activates the light sources 78 according to the received switch position signal. The processor unit 102 later also receives light intensity measurements from the photodetector 21 after a predetermined period. The processor unit 102 then determines a gemstone test result in accordance to the light intensity measurements.

The processor unit 102 transmits an electrical signal regarding the determined gemstone test result to the indicator lights 89. The processor unit 102 can also send a corresponding signal to the buzzer 92.

The processor unit 102 monitors the output voltage of the battery module 105 and provides an alert signal to the low battery indicator 108. The low battery indicator 108 then emits a corresponding light to the user.

The handheld casing 13 acts to contain and protect parts of the gemstone testing apparatus, including the light module 19, the test probe 16, the power source unit 33 and the electronic testing unit 28 and the display unit 30.

The hollow conical member 42 of the head portion 38 is used for containing and protecting the light sources 78, the test probe 16, the photodetector 21 and a part of the electronic testing unit 28.

The elongated hollow body portion 36 is provided for containing and protecting the pressure switch, the display unit 30, the power source unit 33 and a part of the electronic testing unit 28.

The gemstone testing apparatus 10 provides several benefits.

The two light sources 78 enable the table 120a of the specimen 120 to receive sufficient light rays from the light sources 78, even when the metal tube 68 is placed at different parts of the table 120a, such as an edge of the table 120a.

In use, the specimen 120 is often small. Because of this, a user may place the metal tube 68 at different parts of the table 120a of the specimen 120. For example, the metal tube 68 can be placed near to a center location of the table 120a of the specimen 120. It can also be placed at an edge of the table 120a. In spite of this, the two light sources 78 enable the specimen 120 to receive enough light rays for testing the specimen.

The length of the metal tube 68 prevents the metal tube 68 from being easily bent. A distance between the first end 68a of the metal tube 68 and the light sources 78 is also short enough to enable light rays from the light sources 78 to reach the specimen 120 with no or little loss of light rays, thereby not reducing light intensity.

In a general sense, the indicator lights 89 can be replaced by a display panel, such as a color or a monochrome screen display, which can be provided by a Liquid Crystal Display (LCD) or an Organic Light-Emitting Diode (OLED) display.

The handheld casing 13 can comprise a catch which allows an external cap 121 to be attached to the handheld casing 13 using a snap-fit mechanism. The external cap 121 is used for protecting the test probe 16 from being damaged.

As shown in FIGS. 9 and 11, the external cap 121 can include a gemstone test reference tablet 122. The gemstone test reference tablet 122 is provided on an outer surface 121a of the external cap 121 for easy access. The gemstone test reference tablet 122 includes a layer 122a of transparent material and a layer 122b of reflective material. The transparent material layer 122a is placed next to the reflective material layer 122b while the reflective material layer 122b is placed next to the outer surface 121a of the external cap 121.

A user may use the gemstone test reference tablet 122 to check functions of the gemstone testing apparatus 10. The user presses the first end 68a of the metal tube 68 of the test probe 16 of the gemstone testing apparatus 10 against the gemstone test reference tablet 122. The reflective material layer 122b then acts to reflect light from the light sources 78 of the gemstone testing apparatus 10, just like a diamond, while the transparent material layer 122a acts to protect the reflective material layer 122b.

The metal tube 68 can be replaced by a light guide, such as a hollow tube, wherein an inner surface of the hollow tube is coated with a reflective layer.

The gemstone testing apparatus 10 can include three or more light sources, instead of just two light sources. These light sources are placed around the metal tube 68 in a symmetric manner. Each of the light sources can be positioned at a predetermined angle with respect to the longitudinal axis of the gemstone testing apparatus 10. The multiple light sources can allow production of light rays with a higher intensity for illuminating the specimen 120.

The light sources can be replaced by a ring light enclosing the test probe 16. The ring light can be configured to emit light rays that are directed to a location near the first end 68a of the metal tube 68. The ring light can also enable production of light rays with a higher intensity for illuminating the specimen 120.

The processor unit 102 comprises a peripheral module that includes a timer. The timer can be programmed or instructed to switch off the electrical power of the gemstone testing apparatus 10, when the electronic testing unit 28 is inactive for a predetermined period. Put differently, the gemstone testing apparatus 10 is automatically powered off when it is not in use for a predetermined period to conserve or save power.

The display unit 30 can include an electrical power indicator for showing that the electronic testing unit 28 is powered on.

FIG. 10 shows a flow chart 130 of a method of operating the gemstone testing apparatus 10.

The flow chart 130 includes a step 133 of a user providing a specimen 120.

The user then presses the metal tube 68 of the gemstone testing apparatus 10 against the specimen, in a step 136. The metal tube 68 is placed such that it is about at right angle with respect to the table 120a of the specimen 120.

This later causes the micro-switch 52 to be placed, from its open position, to the closed position, in a step 140. The micro-switch 52 also provides a switch position signal to the processor unit 102.

The processor unit 102 activates the multiple light sources and provides electrical current to the multiple light sources 78, in a step 143.

The activated multiple light sources 78 afterward produces ultraviolet light rays to illuminate the specimen 120, in a step 146.

The metal tube 68 subsequently directs these light rays to the second end 68b of the metal tube 68 and to the photodetector 21, in a step 149.

The photodetector 21 then measures intensity of light rays being reflected from the specimen 120, in a step 152.

The processor unit 102 then determines a gemstone test result in accordance to the light intensity measurements. The processor unit 102 transmits an electrical signal regarding the determined gemstone test result to the indicator lights 89 and to the buzzer 92, in a step 155.

The indicator lights 89 receives the electrical signal regarding a gemstone test result from the processor unit 102 and then emits a corresponding light for showing the gemstone test result to the user, in a step 160.

The buzzer 92 also receives the electrical signal from the processor unit 102 and then produces a corresponding audio sound according to the gemstone test result, in a step 163.

The embodiments can also be described with the following lists of features or elements being organized into an item list. The respective combinations of features, which are disclosed in the item list, are regarded as independent subject matter, respectively, that can also be combined with other features of the application.

1. A gemstone testing apparatus for testing a gemstone specimen, the gemstone testing apparatus comprising
   a handheld casing,
   a plurality of light sources,
   a test probe being placed at one end of the handheld casing,
   a first end of the test probe is placed outside the handheld casing, the plurality of light sources is provided for emitting light rays towards an area that is in the vicinity of the first end, and the first end is adapted for receiving light rays from the specimen and for transmitting the light rays to a second end of the test probe,
   a photodetector, the photodetector being arranged to measure an intensity of the light rays from the second end,
   a processor unit for determining a material of the specimen in accordance to a measurement of the intensity of the light rays, and
   a display unit for displaying the gemstone test result, wherein
   the plurality of light sources is provided on at least two sides of the test probe.
2. The gemstone testing apparatus according to item 1, wherein
   the plurality of light sources comprises two light sources.
3. The gemstone testing apparatus according to item 1 or 2, wherein
   the plurality of light sources is arranged around the test probe in a symmetric manner.
4. The gemstone testing apparatus according to one of the preceding items further comprising
   a pressure switch, and
   a pressure transmitting means for transferring a force from the test probe to the pressure switch, wherein the pressure switch activates the gemstone testing apparatus.
5. The gemstone testing apparatus according to item 4, wherein
   the pressure switch comprises a micro-switch.
6. The gemstone testing apparatus according to one of the preceding items, wherein
   the plurality of light sources emits light rays with a wavelength between about 315 nm and about 400 nm.
7. The gemstone testing apparatus according to item 6, wherein
   the plurality of light sources emits light rays with a wavelength of about 365 nm.
8. The gemstone testing apparatus according to one of the preceding items, wherein
   the plurality of light sources comprises a ring light being provided to surround the test probe.
9. The gemstone testing apparatus according to one of the preceding items further comprising
   an external cap being attachable to the handheld casing for protecting the test probe.
10. The gemstone testing apparatus according to item 9, wherein
    the external cap comprises a gemstone test reference tablet that is provided for checking functions of the gemstone testing apparatus.
11. The gemstone testing apparatus according to one of the preceding items further comprising
    a power source unit for supplying electrical power to the gemstone testing apparatus
12. The gemstone testing apparatus according to one of the preceding items, wherein
    the display unit comprises a plurality of indicator lights for providing visual indications of the gemstone test result.
13. The gemstone testing apparatus according to one of the preceding items further comprising
    a buzzer for providing an audio indication of the gemstone test result.
14. The gemstone testing apparatus according to one of the preceding items, wherein
    the test probe comprises a hollow light guide with a reflective inner surface.
15. The gemstone testing apparatus according to item 14, wherein
    the light guide comprises a metal tube.
16. A method for differentiating between a diamond and a moissanite, the method comprising
    pressing a test probe of a gemstone testing apparatus against a gemstone specimen,
    transmitting a force from the test probe to a pressure switch of the gemstone testing apparatus,
    activating a plurality of light sources of the gemstone testing apparatus for illuminating the gemstone specimen,
    wherein the gemstone specimen receives light rays from at least one light source,
    measuring an intensity of the light rays being reflected from the gemstone specimen, and
    determining a material of the gemstone specimen in accordance to the measured light intensity.
17. The method according to item 16 further comprising providing an indication of the material of the gemstone specimen to a user.
18. The method according to item 17, wherein the provision of the indication of the material of the gemstone specimen comprises providing a visual indication of the material of the gemstone specimen.
19. The method according to item 17 or 18, wherein the provision of the indication of the material of the gemstone specimen comprises providing an audio indication of the material of the gemstone specimen.

Although the above description contains much specificity, these should not be construed as limiting the scope of the embodiments but merely providing illustration of the foreseeable embodiments. Especially the above stated advantages of the embodiments should not be construed as limiting the scope of the embodiments but merely to explain possible achievements if the described embodiments are put into practise. Thus, the scope of the embodiments should be determined by the claims and their equivalents, rather than by the examples given.

REFERENCE NUMBERS 10 gemstone testing apparatus
13 elongated handheld casing
16 test probe
19 light module
21 photodetector
25 pressure switch
28 electronic testing unit
30 display unit
33 power source unit
36 elongated hollow body portion
36a first end of the elongated hollow body portion
36b second end of the elongated hollow body portion
38 head portion
40 spring support unit
42 hollow conical member of the head portion
44 actuator member of the head portion
47 support member
50 coil torsion springs
52 mechanical micro-switch
55 rectangular body
57 offset lever
59 single throw and single pole (STSP) switch
62 electrical terminals
65 on/off button
68 metal tube
68a first end of the metal tube
68b second end of the metal tube
70 reflective inner surface
74 protective shell
76 cavity formed by the protective shell
78 light sources
78' border of light rays
84 photodiode
89 indicator lights
92 buzzer
96 current limiting resistors
102 processor unit
105 battery module
107 voltage regulator
108 low battery indicator
110 power socket connector
112 battery charger
114 external power source
120 specimen
120a table of the specimen
120b side facet of the specimen
121 external cap
121a outer surface
122 gemstone test reference tablet
122a layer
122b layer
130 flow chart
133 step
136 step
140 step
143 step
146 step
149 step
152 step
155 step
160 step
163 step

The invention claimed is:

1. A hand-held gemstone testing apparatus comprising:
an elongated handheld body extending along a longitudinal axis from a body proximal end to a body distal end;
a test probe disposed at the body proximal end and comprising a tubular optical transmission channel extending along the longitudinal axis from a tubular channel proximal end to a tubular channel distal end, wherein the tubular channel proximal end is configured to engage with a gemstone test specimen for gemstone testing;
a light module comprising a UV light source at the body proximal end wherein the light module is configured to emit UV light in a proximal direction away from the elongated handheld body towards the gemstone test specimen when the gemstone test specimen is engaged with the tubular channel proximal end;
a photodetector in optical communication with the tubular optical transmission channel and configured to receive the UV light emitted from the UV light source after the UV light has reflected from the gemstone test specimen as the gemstone test specimen is engaged with the tubular channel proximal end;
an electronic testing system comprised in the elongated handheld body, operably coupled to the photodetector, and operably coupled to the light module to activate the UV light source; and,
a display interface disposed at an external surface of the elongated handheld body and configured to display a gemstone test result generated by the electronic testing system when in operation; and,
a cover to protect the test probe.

2. The hand-held gemstone testing apparatus of claim 1, wherein the tubular channel proximal end is fixedly disposed at the body proximal end.

3. The hand-held gemstone testing apparatus of claim 1, wherein the light module is fixedly disposed at the body proximal end.

4. The hand-held gemstone testing apparatus of claim 1, wherein the light module is configured to emit UV light to illuminate the gemstone test specimen when the gemstone test specimen is engaged with the tubular channel proximal end.

5. The hand-held gemstone testing apparatus of claim 1, wherein the UV light source comprise a plurality of UV light sources.

6. The hand-held gemstone testing apparatus of claim 5, wherein the plurality of UV light sources comprise a first UV light source and a second UV light source, with the first UV light source laterally opposed to the second UV light source about the longitudinal axis, and wherein each of the plurality of UV light sources comprises a respective optical axis, each optical axis being angled and directed toward the tubular channel proximal end.

7. The hand-held gemstone testing apparatus of claim 1, wherein to activate the UV light source comprises to control a UV light level of the UV light source.

8. The hand-held gemstone testing apparatus of claim 1, wherein the cover comprises a body proximal end cap configured to couple to the elongated handheld body and operable to cap off the body proximal end.

9. The hand-held gemstone testing apparatus of claim 1, wherein the cover comprises an external cap.

10. The hand-held gemstone testing apparatus of claim 1, wherein, in a gemstone testing operation,
the tubular channel proximal end is engaged with a first specimen; and,
the photodetector receives UV light emitted from the UV light source after the UV light has reflected from the first specimen as the first specimen is engaged with the tubular channel proximal end.

11. The hand-held gemstone testing apparatus of claim 1, wherein when the gemstone test specimen is engaged with the tubular channel proximal end, the gemstone test specimen is placed on a first surface such that the longitudinal axis of the elongated handheld body is oriented substantially orthogonal to the first surface.

12. The hand-held gemstone testing apparatus of claim 1, wherein the electronic testing system comprises a computer system configured to identify a type of a gemstone to generate the gemstone test result.

13. The hand-held gemstone testing apparatus of claim 1, wherein the gemstone test result comprises a detection of a moissanite.

14. The hand-held gemstone testing apparatus of claim 1, wherein the electronic testing system is configured to generate the gemstone test result as a function of an UV absorbance of the gemstone test specimen.

15. The hand-held gemstone testing apparatus of claim 1, wherein the photodetector is configured to measure an UV absorbance of the UV light at the gemstone test specimen.

16. The hand-held gemstone testing apparatus of claim 1, wherein the gemstone test result comprises an audio indication of a type of the gemstone test specimen.

17. The hand-held gemstone testing apparatus of claim 16, further comprising a buzzer configured to generate the audio indication.

18. The hand-held gemstone testing apparatus of claim 16, wherein the audio indication comprises a beeping sound.

19. The hand-held gemstone testing apparatus of claim 1, wherein the external surface of the elongated handheld body further comprises a user interface configured to activate the hand-held gemstone testing apparatus for the gemstone testing.

20. The hand-held gemstone testing apparatus of claim 19, wherein the user interface comprises an on/off button disposed on an outer surface of the elongated handheld body.

21. The hand-held gemstone testing apparatus of claim 1, further comprising a battery configured to provide electrical power to the hand-held gemstone testing apparatus.

22. The hand-held gemstone testing apparatus of claim 21, further comprising a power connector operably coupled to the battery, wherein the power connector is reliably coupled to a battery charger such that the battery is rechargeable.

23. The hand-held gemstone testing apparatus of claim 21, further comprising a low battery indicator disposed on an outer surface of the elongated handheld body, wherein the low battery indicator is configured to provide an alert signal when the battery is low in power.

24. The hand-held gemstone testing apparatus of claim 1, wherein the display interface comprises an OLED illumination.

25. A hand-held gemstone testing apparatus comprising:
an elongated handheld body extending along a longitudinal axis from a body proximal end to a body distal end;
a test probe disposed at the body proximal end and comprising a tubular optical transmission channel extending along the longitudinal axis from a tubular channel proximal end to a tubular channel distal end, wherein the tubular channel proximal end is configured to engage with a gemstone test specimen for gemstone testing;
a light module comprising a plurality of UV light sources at the body proximal end and the light module is configured to emit UV light in a proximal direction away from the elongated handheld body towards the gemstone test specimen when the gemstone test specimen is engaged with the tubular channel proximal end;
a photodetector in optical communication with the tubular optical transmission channel and configured to receive the UV light emitted from the plurality of UV light sources after the UV light has reflected from the gemstone test specimen as the gemstone test specimen is engaged with the tubular channel proximal end;
an electronic testing system comprised in the elongated handheld body, operably coupled to the photodetector, and operably coupled to the light module to activate the plurality of UV light sources, wherein the electronic testing system comprises a computer system configured to identify a type of a gemstone to generate a gemstone test result as a function of an UV absorbance of the gemstone test specimen; and,
a display interface comprising an OLED illumination, disposed at an external surface of the elongated handheld body and configured to display the gemstone test result generated by the electronic testing system when in operation, wherein the gemstone test result comprises a detection of a moissanite; and,
a buzzer configured to generate an audio indication indicating the gemstone test result.

26. The hand-held gemstone testing apparatus of claim 25, wherein the tubular channel proximal end is fixedly disposed at the body proximal end.

27. The hand-held gemstone testing apparatus of claim 25, wherein the light module is fixedly disposed at the body proximal end.

28. The hand-held gemstone testing apparatus of claim 25, wherein the light module is configured to emit UV light to illuminate the gemstone test specimen when the gemstone test specimen is engaged with the tubular channel proximal end.

29. The hand-held gemstone testing apparatus of claim 25, wherein the plurality of UV light sources comprises a first UV light source and a second UV light source, with the first UV light source laterally opposed to the second UV light source about the longitudinal axis, and wherein each of the plurality of UV light sources comprises a respective optical axis, each optical axis being angled and directed toward the tubular channel proximal end.

30. The hand-held gemstone testing apparatus of claim 25, wherein to activate the plurality of UV light sources comprises to control a UV light level of the plurality of UV light sources.

31. The hand-held gemstone testing apparatus of claim 25, further comprising a cover to protect the test probe.

32. The hand-held gemstone testing apparatus of claim 31, wherein the cover comprises a body proximal end cap configured to couple to the elongated handheld body and operable to cap off the body proximal end.

33. The hand-held gemstone testing apparatus of claim 31, wherein the cover comprises an external cap.

34. The hand-held gemstone testing apparatus of claim 25, wherein, in a gemstone testing operation,
the tubular channel proximal end is engaged with a first specimen; and, the photodetector receives UV light emitted from the plurality of UV light sources after the UV light has reflected from the first specimen as the first specimen is engaged with the tubular channel proximal end.

35. The hand-held gemstone testing apparatus of claim 25, wherein when the gemstone test specimen is engaged with the tubular channel proximal end, the gemstone test specimen is placed on a first surface such that the longitudinal axis of the elongated handheld body is oriented substantially orthogonal to the first surface.

36. The hand-held gemstone testing apparatus of claim 25, wherein the photodetector is configured to measure the UV absorbance of the UV light at the gemstone test specimen.

37. The hand-held gemstone testing apparatus of claim 25, wherein the audio indication comprises a beeping sound.

38. The hand-held gemstone testing apparatus of claim 25, wherein the external surface of the elongated handheld body further comprises a user interface configured to activate the hand-held gemstone testing apparatus for the gemstone testing.

39. The hand-held gemstone testing apparatus of claim 38, wherein the user interface comprises an on/off button disposed on an outer surface of the elongated handheld body.

40. The hand-held gemstone testing apparatus of claim 25, further comprising a battery configured to provide electrical power to the hand-held gemstone testing apparatus.

41. The hand-held gemstone testing apparatus of claim 40, further comprising a power connector operably coupled to the battery, wherein the power connector is reliably coupled to a battery charger such that the battery is rechargeable.

42. The hand-held gemstone testing apparatus of claim 40, further comprising a low battery indicator disposed on an outer surface of the elongated handheld body, wherein the low battery indicator is configured to provide an alert signal when the battery is low in power.

43. A hand-held gemstone testing apparatus comprising:
an elongated handheld body extending along a longitudinal axis from a body proximal end to a body distal end;
a test probe disposed at the body proximal end and comprising a tubular optical transmission channel extending along the longitudinal axis from a tubular channel proximal end to a tubular channel distal end, wherein the tubular channel proximal end is configured to engage with a gemstone test specimen for gemstone testing;
a light module comprising a plurality of UV light sources at the body proximal end and the light module is configured to emit UV light in a proximal direction away from the elongated handheld body towards the gemstone test specimen when the gemstone test specimen is engaged with the tubular channel proximal end;
a photodetector in optical communication with the tubular optical transmission channel and configured to receive the UV light emitted from the plurality of UV light sources after the UV light has reflected from the gemstone test specimen as the gemstone test specimen is engaged with the tubular channel proximal end;
an electronic testing system comprised in the elongated handheld body, operably coupled to the photodetector, and operably coupled to the light module to activate the plurality of UV light sources; and,
a display interface disposed at an external surface of the elongated handheld body and configured to display a gemstone test result generated by the electronic testing system when in operation;
a battery configured to provide electrical power to the test probe; and
a low battery indicator disposed on an outer surface of the elongated handheld body, wherein the low battery indicator is configured to provide an alert signal when the battery is low in power; and,
a cover to protect the test probe,
wherein, in a gemstone testing operation of a first specimen,
the first specimen is engaged with the tubular channel proximal end when the first specimen is placed on a first surface such that the longitudinal axis of the elongated handheld body is oriented substantially orthogonal to the first surface,
the tubular channel proximal end is engaged with the first specimen, and,
the photodetector receives UV light emitted from the plurality of UV light sources after the UV light has reflected from the first specimen as the first specimen is engaged with the tubular channel proximal end.

44. The hand-held gemstone testing apparatus of claim 43, wherein the tubular channel proximal end is fixedly disposed at the body proximal end.

45. The hand-held gemstone testing apparatus of claim 43, wherein the light module is fixedly disposed at the body proximal end.

46. The hand-held gemstone testing apparatus of claim 43, wherein the light module is configured to emit UV light to illuminate the gemstone test specimen when the gemstone test specimen is engaged with the tubular channel proximal end.

47. The hand-held gemstone testing apparatus of claim 43, wherein the plurality of UV light sources comprise a first UV light source and a second UV light source, with the first UV light source laterally opposed to the second UV light source about the longitudinal axis, and wherein each of the plurality of UV light sources comprises a respective optical axis, each optical axis being angled and directed toward the tubular channel proximal end.

48. The hand-held gemstone testing apparatus of claim 43, wherein to activate the plurality of UV light sources comprises to control a UV light level of the plurality of UV light sources.

49. The hand-held gemstone testing apparatus of claim 43, wherein the cover comprises a body proximal end cap configured to couple to the elongated handheld body and operable to cap off the body proximal end.

50. The hand-held gemstone testing apparatus of claim 43, wherein the cover comprises an external cap.

51. The hand-held gemstone testing apparatus of claim 43, wherein the electronic testing system comprises a computer system configured to identify a type of a gemstone to generate the gemstone test result.

52. The hand-held gemstone testing apparatus of claim 43, wherein the gemstone test result comprises a detection of a moissanite.

53. The hand-held gemstone testing apparatus of claim 43, wherein the electronic testing system is configured to generate the gemstone test result as a function of an UV absorbance of the gemstone test specimen.

54. The hand-held gemstone testing apparatus of claim 43, wherein the photodetector is configured to measure an UV absorbance of the UV light at the gemstone test specimen.

55. The hand-held gemstone testing apparatus of claim 43, wherein the gemstone test result comprises an audio indication of a type of the gemstone test specimen.

56. The hand-held gemstone testing apparatus of claim 55, further comprising a buzzer configured to generate the audio indication.

57. The hand-held gemstone testing apparatus of claim 55, wherein the audio indication comprises a beeping sound.

58. The hand-held gemstone testing apparatus of claim 43, wherein the external surface of the elongated handheld body further comprises a user interface configured to activate the hand-held gemstone testing apparatus for the gemstone testing operation.

59. The hand-held gemstone testing apparatus of claim 58, wherein the user interface comprises an on/off button disposed on the outer surface of the elongated handheld body.

60. The hand-held gemstone testing apparatus of claim 43, further comprising a power connector operably coupled to the battery, wherein the power connector is reliably coupled to a battery charger such that the battery is rechargeable.

61. The hand-held gemstone testing apparatus of claim 43, wherein the display interface comprises an OLED illumination.

* * * * *